United States Patent [19]

Tepe et al.

[11] 4,201,549

[45] May 6, 1980

[54] SOIL TESTING APPARATUS AND METHOD

[75] Inventors: Walter Tepe, Geisenheim, Fed. Rep. of Germany; Adam J. J. Van Niewenhuizen, Pretoria North, South Africa

[73] Assignee: Dialytic Electrolysis Laboratorium (Proprietary) Limited, Johannesburg, South Africa

[21] Appl. No.: 913,640

[22] Filed: Jun. 8, 1978

[51] Int. Cl.² .......................................... G01N 33/24
[52] U.S. Cl. ............................. 23/230 R; 47/1 R; 422/68; 422/102
[58] Field of Search ................ 422/56, 57, 58, 102, 422/68; 23/230 R; 47/1 R

[56] References Cited

U.S. PATENT DOCUMENTS

| 3,572,997 | 3/1971 | Burk | 422/61 |
| 3,881,873 | 5/1975 | Klowden | 422/56 |
| 4,126,417 | 11/1978 | Edwards | 422/56 |

*Primary Examiner*—R. E. Serwin
*Attorney, Agent, or Firm*—Ladas, Parry, Von Gehr, Goldsmith & Deschamps

[57] ABSTRACT

Soil testing apparatus comprising two dialytic tubes, one of the tubes containing a dialyzable solution containing H-ions and the other tube containing a dialyzable solution containing carbonate ($CO_3$)ions. The invention also concerns a method of testing a soil sample using such an apparatus.

8 Claims, 1 Drawing Figure

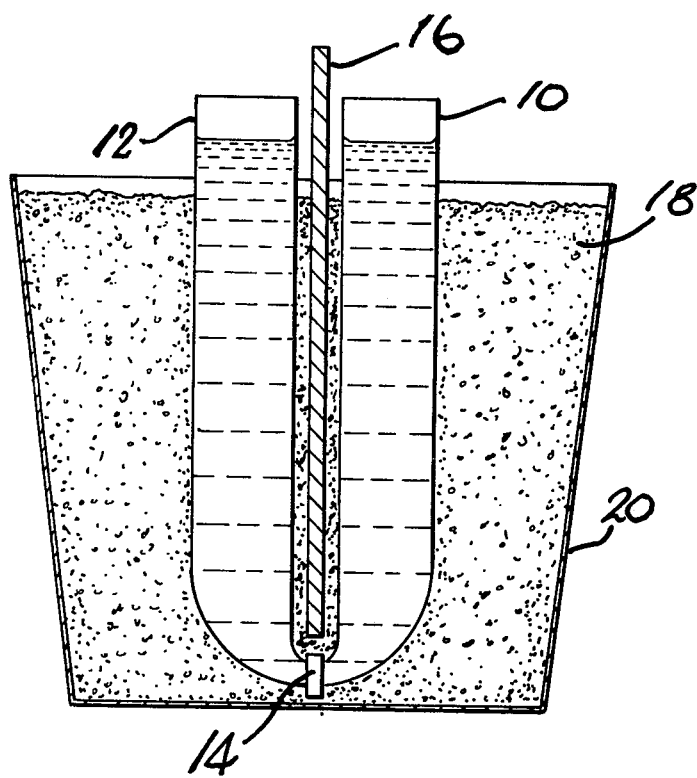

4,201,549

SOIL TESTING APPARATUS AND METHOD

THE PRESENT INVENTION relates to a soil testing apparatus, and to its use for testing the soil with a view to improving the soil.

BACKGROUND OF THE INVENTION

Electrochemical devices for chemical analysis are known, eg from U.S. Pat. Nos. 2,913,386; 822,175 and 3,593,119. Electrochemical devices have been used for analysis of the soil and reference may be had to German Offenlegungsschrift 2,108,642 (Tepe) and 2,326,645. These devices suffer from the disadvantage that they are devices working on the principle of dialysing electrolysis.

It is an object of the invention to provide a method and apparatus for the analysis of soil and which avoids the disadvantages of having to provide a source of electric current.

SUMMARY OF THE INVENTION

The present invention provides a soil testing apparatus comprising two dialytic tubes one of said tubes containing a dialysable solution containing H-ions and the other of the two tubes containing a dialysable solution containing carbonate ($CO_3$) ions. The two tubes are hereinafter referred to as a dialysis unit. The tubes conveniently can be positioned in a soil sample in a container provided for that purpose and/or in situ in a field under investigation.

The invention has the advantage over the prior art that a source of electrical supply is not needed. Thus, the apparatus is convenient to use in the field.

Conveniently, one tube contains a weak acid such as acetic acid and the other tube contains a salt of a weak acid such as aqueous lithium carbonate solution. Dialytic tubes are tubes which are adapted to contain dialysable solution and to permit at least one ion to pass through the tubes into a surrounding medium. Such tubes are commercially available and can be cut to the desired length.

The dialysis unit may be formed from a single length of longer dialytic tube by folding the tube, at a position towards its mid point, back on itself and retaining the fold in the tube. If necessary, the folded part of the tube can have a clip fitted over it to prevent the two solutions mixing with each other. Conveniently, a liquid-impermeable membrane is present between the two tubes. The material known by the Trade Mark 'Plexiglass' can be used to make an impermeable membrane.

The apparatus of the invention may be provided as a kit of parts comprising a packet containing either two dialytic tubes or a length of dialytic tube capable of being folded to make two tubes, and a set of instructions for making up and using a soil testing apparatus. The kit may also include a container for receiving the soil sample, and/or supplies of the dialysable solution.

The invention further provides a method of testing a soil sample, which comprises taking at least two samples of the soil to be tested, placing the samples in separate containers, adding a nutrient medium of known content to one of the samples, inserting the dialysis unit in each container, one of said tubes of the dialysis unit containing a dialysable solution having H-ions therein and the other of the said tubes containing a dialysable solution having carbonate ions therein, leaving the containers for a predetermined time for dialysis to take place, and thereafter analysing the solutions.

The difference in the analysis for the respective solutions between the two containers will indicate the ions which have passed through the walls of the dialytic tubes, the amounts dialysed and the direction in which particular ions have passed. It is then possible to calculate from tables the paucity or excess of certain ions in the samples.

Thus, analysis of the solutions of the testing apparatus enables one to obtain values for the nutrient activity of the soil, the efficiency of fertilisers and the density of the nutrient in the soil.

The invention enables one to improve soil by testing the soil by the method described herein, calculating the excess and/or deficient elements in the soil and indicating the measures to be taken to bring the soil to an optimum condition, for example by adding the elements required in amounts calculated from the results obtained.

The sample of the soil may be taken, with an auger, from beneath the surface level and transferred to a watertight sample container, e.g. a bag of plastics material, and labelled. Stones larger than 1 cm can be removed. If it is clay soil, it may be dried before further handling. If the soil is too dry, it may be wetted with distilled water.

DESCRIPTION OF THE DRAWINGS

The FIGURE of the drawing shows a soil testing apparatus according to the invention, in cross-section.

DETAILED DESCRIPTION OF THE PREFERRED EMBODIMENT

A dialysis tube is folded in half to form two half tubes 10,12. A clip 14 is provided over the bottom end. A liquid-impermeable sheet 16 is provided between the tubes 10 and 12. The tubes 10,12 are inserted in a soil sample 18 in a container 20.

The method of testing may be carried out as follows:

Two soil samples are placed in separate containers, each containing a dialysis unit. One dialysis tube of each unit contains lithium carbonate and the other contains acetic acid. Before placing one of the two samples in a container, a standard nutrient medium is mixed therewith. The containers are then covered to limit evaporation. After a predetermined time, eg 24 hours, the dialysis units are removed, soil is washed therefrom and the solutions analysed quantitatively.

In calculating the results, we have found it convenient to use the following abbreviations for each element compound or ion which was present in the standard nutrient:

$f_a$ is the coefficient of the activity of each element in water and is the average activity of the salt used. This value is available from textbooks.

$f_b$ is the factor for the activity of a certain element in the soil.

DU value = Dialysis unit value.

WV = water value

The following are examples of values of $f_a$ and WV which are available from textbooks.

TABLE

|  | $f_a$ | WV in mg/liter |
| --- | --- | --- |
| $K_2O$ | 0,9 | 132 |
| $Na_2O$ | 0,9 | 43 |
| Mg | 0,7 | 25 |
| $P_2O_5$ | 0,9 | 160 |

TABLE-continued

|  | $f_a$ | WV in mg/liter |
|---|---|---|
| NH$_4$ nitrogen | 0,7 | 35 |
| SO$_4$ | 0,9 | 350 |
| Fe | 0,9 | 11 |
| Mn | 0,9 | 11 |
| Zn | 0,9 | 11,4 |
| Ni | 0,9 | 10 |
| B | 0,9 | 4,3 |
| Cu | 0,9 | 20 |
| Mo | 0,9 | 3 |

The following non-limiting Example illustrates the invention.

EXAMPLE

The apparatus illustrated in the accompanying drawing was used.

As shown in this drawing, a dialysis unit was made by folding a dialysis tube as sold by Hoechst in half to form two half tubes 10, 12. A clip 14 was placed over the fold to maintain it, and a sheet 16 of plexiglass was inserted between the two half tubes 10, 12. Another identical dialysis unit was also made. The effective surface area of each half tube 10, 12 was 120 cm$^2$ and their wall thickness was 0.1 mm.

Two 300 ml soil samples 18 were then taken from between 10 and 40 cm beneath the earth surface. The dialysis units were then placed in separate containers 20 and the samples 18 were respectively firmed around the dialysis units as shown in the drawing. The half tubes of each dialysis unit are, when necessary, clipped together by a rubber band or the like (not shown) to maintain them in side by side relationship as shown in the drawing.

25 ml of lithium carbonate solution (0.01 N) was inserted into each half tube 10, and 25 ml of acetic acid (0.1 N) was inserted into each half tube 12.

Sufficient distilled water was then added to one sample (container 1) to saturate it, and the amount of distilled water was noted ("x" ml). 20 ml of a standard balanced nutrient medium of 15 elements was added to the other sample (container 2) followed by ("x" −20) ml of distilled water.

An empty beaker was inverted over each of the two containers and dialysis was then allowed to take place for 24 hours. After 24 hours the dialysis units were removed and washed externally and the contents of the dialysis units were tipped into bottles and analysed.

As a control a third dialysis unit was placed in a container having 280 ml distilled water and 20 ml of the nutrient medium therein and dialysis was similarly permitted for 24 hours.

In a typical example the following results were obtained using the above procedure for K$_2$O.

1. The control container contained 280 ml distilled water and 20 ml of the said nutrient medium. The measured DU value=132 mg K$_2$O/liter water (H$_2$O)=water value (WV) (See also the Table above).

2. Container 1 contained 300 ml soil saturated with "x" ml distilled water (H$_2$O). The measured DU value=30 mg K$_2$O/liter soil. This value is referred to as "a" below.

3. Container 2 contained 300 ml soil plus ("x" −20) ml water (H$_2$O) and 20 ml of the nutrient medium. The measured DU value=80 mg K$_2$O/liter soil. This value is referred to as "b" below. The $f_b$ value (activity factor) was then obtained from the formula $$f_b = \frac{("b" - "a") \times f_a}{WV}$$
$$= \frac{(80 - 30) \times 0.9}{132} \text{ (See Table above)}$$
$$= 0.34$$

The value "a" of 30 mg K$_2$O/liter soil is known as the activity of the K$_2$O in the soil and the density "d" of K$_2$O in the soil was calculated from the formula:

"d"="a"/$f_b$=30/0.34=88.2 mg k$_2$O/liter soil

With the present invention values can be obtained for 15 nutrient elements, in a single extraction. These values are true for all substrates and soil conditions. For the first time, it is possible to calculate the activity of the ions by comparing the ion-diffusion in water and in the soil.

We claim:

1. A soil testing apparatus comprising a container containing a sample of soil to be tested, and two dialytic tubes positioned in the container, the said tubes being closed at their lower ends to permit the tubes to contain liquid and open at their upper ends, the lower ends of the tubes being positioned beneath the surface of the soil, one of said tubes containing a dialysable solution containing hydrogen ions and the other tube containing a dialysable solution containing carbonate ions, whereby samples of the said solutions may be removed from the upper ends of the tubes and analysed after dialysis has taken place.

2. An apparatus according to claim 1, wherein one tube contains acetic acid.

3. An apparatus according to claim 2, wherein the other tube contains lithium carbonate solution.

4. A soil testing apparatus according to claim 1, wherein the two tubes are formed from a longer length of dialytic tube by folding the longer length of tube, at a position towards its mid point, and clipping the folded parts together.

5. A soil testing apparatus according to claim 1, wherein a liquid-impermeable membrane is present between the two tubes.

6. A soil testing apparatus according to claim 4, wherein a liquid-impermeable membrane is present between the two tubes.

7. A method of testing a soil sample, which comprises
   (i) taking at least two samples of the soil to be tested,
   (ii) placing the samples in spearate containers,
   (iii) adding a nutrient medium of known content to one of the samples,
   (iv) inserting two dialytic tubes in each container, the said tubes being closed at their lower ends to permit the tubes to contain liquid and open at their upper ends, the lower ends of the tubes being positioned beneath the surface of the soil, one of said tubes containing a dialysable solution containing hydrogen ions and the other of the said tubes containing a dialysable solution containing carbonate ions,
   (v) leaving the containers for a predetermined time for dialysis to take place, and
   (vi) thereafter analysing the solutions according to established chemical methods to establish the presence and amount of nutrient ions in the soil after removing the solutions through the open ends of the tubes for analysis.

8. A method of improving soil which comprises
(i) taking at least two samples of the soil to be tested,
(ii) placing the samples in separate containers,
(iii) adding a nutrient medium of known content to one of the samples,
(iv) inserting two dialytic tubes in each container, the said tubes being closed at their lower ends to permit the tubes to contain liquid and open at their upper ends, the lower ends of the tubes being positioned beneath the surface of the soil, one of said tubes containing a dialysable solution containing hydrogen ions and the other of the said tubes containing a dialysable solution containing carbonate ions,
(v) leaving the containers for a predetermined time for dialysis to take place,
(vi) removing samples of the solutions through the open ends of the tubes and analysing the solutions, according to established chemical methods, to find the activity of the ions in the soil,
(vii) calculating from the analysis those elements in which the soil is deficient and by what amounts it is deficient, and
(viii) adding those elements in about those amounts to the soil.

* * * * *